United States Patent
Rajapakse et al.

(10) Patent No.: US 10,672,501 B2
(45) Date of Patent: Jun. 2, 2020

(54) CONTROL APPROACH TO CELL REPROGRAMMING

(71) Applicant: THE REGENTS OF THE UNIVERSITY OF MICHIGAN, Ann Arbor, MI (US)

(72) Inventors: Indika Rajapakse, Ann Arbor, MI (US); Geoff Patterson, Ann Arbor, MI (US); Scott Ronquist, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 342 days.

(21) Appl. No.: 15/678,142

(22) Filed: Aug. 16, 2017

(65) Prior Publication Data
US 2018/0129775 A1    May 10, 2018

Related U.S. Application Data
(60) Provisional application No. 62/377,050, filed on Aug. 19, 2016.

(51) Int. Cl.
| | |
|---|---|
| *G01N 33/48* | (2006.01) |
| *G01N 33/50* | (2006.01) |
| *G16B 5/00* | (2019.01) |
| *C12N 5/071* | (2010.01) |
| *G16B 25/00* | (2019.01) |
| *C12Q 1/6881* | (2018.01) |

(52) U.S. Cl.
CPC ............ *G16B 5/00* (2019.02); *C12N 5/0602* (2013.01); *C12Q 1/6881* (2013.01); *G16B 25/00* (2019.02); *C12N 2501/60* (2013.01); *C12N 2506/09* (2013.01); *C12Q 2600/158* (2013.01)

(58) Field of Classification Search
None
See application file for complete search history.

(56) References Cited

U.S. PATENT DOCUMENTS
2006/0046249 A1 *  3/2006  Huang ................ C12Q 1/6886
                                                                 435/6.14

OTHER PUBLICATIONS
Rajapakse et al "On Emerging Nuclear Order" J. Cell Biol. vol. 192, No. 5 (Mar. 7, 2011).
Rajapakse et al "Dynamics and Control of State-Dependent Networks for Probing Genomic Organization", PNAS (Oct. 18, 2011).
Ronquist et al "Algorithm for Cellular Reprogramming", PNAS (Nov. 7, 2017).
Cahan et al "CellNet: Network Biology Applied to Stem Cell Engineering", Cell (158(4), pp. 903-915 (2014).
Rackham et al "A Predictive Computational Framework for Direct Reprogramming Between Human Cell Types", National Genetics 48, pp. 331-335 (2015).
D'Alessio et al "A Systematic Approach to Identify Candidate Transcription Factors That Control Cell Identity", Stem Cell Reports 5(5), pp. 763-765 (2015).
Ding et al "Recipes and Mechanisms of Cellular Reprogramming: A Case Study on Budding Yeast *Saccharomyces cerevisiae*", BMC Systems Biology 5(50) (2011).
Crespo et al "A General Strategy for Cellular Reprogramming: The Importance of Transcription Factor Cross-Repression" Stem Cells 31(10), pp. 2127-2135 (2013).
Chen, et al "Functional Organization of the Human 4D Nucleome" PNAS, vol. 223, No. 26 (2015).

* cited by examiner

*Primary Examiner* — Russell S Negin
(74) *Attorney, Agent, or Firm* — Harness, Dickey & Pierce, P.L.C.

(57) ABSTRACT

A method is presented for reprogramming cells of a subject. As a starting point, a biological sample of a sample cell is received from the subject, where the sample cell has a given cell type. The method includes: determining gene expression data for the sample cell from the biological sample; receiving gene expression data for a target cell having a target cell type, where the target cell type differs from the given cell type; deriving a state transition matrix which models cell dynamics; computing a regulatory set for a given transcription factor, where the regulatory set quantifies influence of the given transcription factor on a genome; expressing reprogramming of the sample cell to the target cell with a state-space representation of a linear system; and solving for the input vector in the state-space representation.

15 Claims, 3 Drawing Sheets

CONTROL APPROACH TO CELL REPROGRAMMING

CROSS-REFERENCE TO RELATED APPLICATIONS

This application claims the benefit of U.S. Provisional Application No. 62/377,050, filed on Aug. 19, 2016. The entire disclosure of the above application is incorporated herein by reference.

GOVERNMENT CLAUSE

This invention was made with government support under D15AP00007 awarded by the Department of the Interior and Department of the Interior (direct) D15AP00007/DARPA (Prime). The Government has certain rights in this invention.

FIELD

The present disclosure relates to a control approach for cell reprogramming.

BACKGROUND

In vitro, human skin cells can be converted to several other cell types by introducing, in excess, certain proteins which are naturally present in some human cell. As the skin cells progress through the cell cycle, they update these exogenous proteins which bind to the cell's DNA and orchestrate the structural and functional changes which alter the cell's identity. These binding proteins, transcription factors, are necessary for a variety of natural cellular functions and many of them have been characterized and used in cell type conversions.

Manually directed conversion between cell types outside of the natural cell progression, or reprogramming, was first demonstrated in 1989 by Harold Weintraub et al., who reprogrammed human skin cells into muscle cells by over-expressing one particular protein. In 2006, Shinya Yamanaka et al reprogrammed human skin cells to stem cells using the combination of four proteins. Since then a wide-variety of other cell type conversions have been discovered and confirmed in the laboratory setting. Together, these discoveries have given credence to the idea that any cell type may have the potential to be reprogrammed to any other cell type given the correct transcription factors, regardless of cell-type differentiation. All of these findings were based on a deep understanding of the function of each protein, the transcription profile of each cell type, and considerable trial and error, particularly in the case of Yamanaka.

In attempting to optimize the efficiency of the reprogramming process, and bypass time-intensive wetlab methods, a computational method has been developed for determining potentially useful transcription factors prior to testing.

This section provides background information related to the present disclosure which is not necessarily prior art.

SUMMARY

This section provides a general summary of the disclosure, and is not a comprehensive disclosure of its full scope or all of its features.

A method is presented for reprogramming cells of a subject. As a starting point, a biological sample of a sample cell is received from the subject, where the sample cell has a given cell type. The method includes: determining gene expression data for the sample cell from the biological sample; receiving gene expression data for a target cell having a target cell type, where the target cell type differs from the given cell type; deriving a state transition matrix which models cell dynamics; computing a regulatory set for a given transcription factor, where the regulatory set quantifies influence of the given transcription factor on a genome; expressing reprogramming of the sample cell to the target cell with a state-space representation of a linear system; and solving for the input vector in the state-space representation. The gene expression data for the sample cell may be RNA-seq data.

In the state-space representation, the gene expression data for the target cell serves as an output vector in the state-space representation, the gene expression data for the sample cell serves as a state vector in the state-space representation, the regulatory set for the given transcription factor serves as an input matrix in the state-space representation, and an input vector in the state-space representation represents the given transcription factor.

In one embodiment, the gene expression data for the cell is determined by grouping genes within same topologically associated domains; and forming the state vector from the grouped genes. The grouping genes within same topologically associated domains may include using chromosome conformation capture techniques.

In some embodiments, the state transition matrix can be derived by selecting a matrix that differs the least from an identity matrix.

In other embodiments, the regulatory set for a given transcription factor is computed by computing a regulator set for each of a plurality of transcription factors and joining the plurality of regulatory sets to form the input matrix.

In yet other embodiments, solving for the input vector includes determining values for the input vector that minimize distance between the sample cell and the target cell, for example using a least squares method.

In one aspect, the state-space representation is defined at two or more discrete times, such that the two or more discrete times signify different points in a cell cycle and the given transcription factor can be introduced into a cell at any of the two or more discrete times. In this case, the input vector is solved for by identifying a subset of transcription factors, determining each possible sequence in which the transcription factors in the subset of transcription factors can be introduced into a cell, and solving for the input vector for each possible sequence of transcription factors in the subset of transcription factors.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

In order to model reprogramming (or any system, for that matter) in a control theoretic framework, two important pieces of information are: (1) knowledge of how the system evolves without inputs, and (2) knowledge of how inputs affect those dynamics. For reprogramming, using expression data to represent the state of a cell, time series RNA-seq data for proliferating skin cells is used to approximate (1). Skin cells are natural choices for the starting cell type in reprogramming although other cell types are also contemplated by this disclosure. Using protein binding data, gene accessibility data, and other existing knowledge about how proteins can affect DNA, one can approximate (2). It is noted that this program is currently set-up for cell-cycle synchronized human fibroblasts as the initial state, though the methods employed can be duplicated with any cultured cell line. Human fibroblasts provide a useful starting point for any reprogramming as they are easily obtained as tissue samples, and many cell-lines can be cultured readily.

By way of background, gene activity data is obtained for fibroblast cells progressing through the cell cycle (RNA-seq, units=reads per kilobase per million, RPKM). Importantly, the population was cell-cycle synchronized prior to data collection, so that all the cells were temporarily held in the first stage of the cell cycle, G0/G1. Upon release into the cell cycle, the population was observed every $\Delta t=8$ hours for 56 hours, yielding M=8 time points (at 0, 8, 16, . . . , 56 hours),
Ñ=22,083 genes
M=8 measurement times.
Let $g_{i,m}$ be the measured activity of gene i=1, . . . , Ñ at measurement time m=1, . . . , M. A summary of our nomenclature is given in Table 1 below.

TABLE 1

Nomenclature

| | |
|---|---|
| $g_{i,m}$ | expression of gene i in measurement m |
| $w_{i,j}$ | regulation weight of TF j on gene i |
| $c_{i,j}$ | # of consensus motifs for TF j within ±5 kb of the TSS for gene i |
| $a_i$ | accessibility (1 or 0) of gene i |
| $x_{k,m}$ | expression of TAD k in measurement m |
| $b_{k,j}$ | regulation of weight of TF j on TAD k |

Analysis of certain cell-cycle marker genes indicate that the synchronized skin cells took between 32-40 hours to complete one cell cycle (FIG. 1). This was longer than expected, but FIG. 1 suggests it took some time for the cell cycle to start after serum introduction. There is no dominant phase for time points 48 and 56, suggesting that the cells have become largely unsynchronized.

For modeled reprogramming, a final integration time of 40 hours is chosen so that the dynamics data is as reliable as possible, and so that the modeled conversions take place over the course of one full cell cycle. Publicly available RNA-seq data was obtained for several other cell types: embryonic stem cells (ESC), myotubes (MT), neurons (NEU), and cardiomyocytes (CM). Each of these datasets were single time point measurements of unsynchronized cells, and therefore represent some average expression over the cell cycle.

A transcription factor (TF) is a DNA binding protein that can regulate a gene positively or negatively, by encouraging (activator) or discouraging (repressor) transcription of that gene when bound near it. This is accomplished, for example, by altering local chromatin conformation or by recruiting RNA polymerase II and other transcriptional machinery. The degree to which a TF activates or represses a gene depends on the specific TF/gene interaction and most likely on a variety of nuclear subtleties and intricacies that are difficult to quantify.

Let $w_{i,j}$ be the theoretical regulation weight of TF j on gene i, where $w_{i,j}>0$ ($w_{i,j}<0$) if TF j activates (represses) gene i. Weights that are bigger in absolute value, $|w_{i,j}|>>0,|$ indicate stronger transcriptional influence, and weights equal to zero, $w_{i,j}=0$, indicate no influence.

Extensive TF perturbation experiments would be needed to determine $w_{i,j}$ for each TF j on each gene i. Instead, this disclosure proposes an alternative method to approximate $w_{i,j}$ from existing, publicly available data for TF consensus binding motifs, gene accessibility, and average activator/ repressor activity. TF binding data was obtained based on consensus motifs for 547 TFs (as identified using hg19 scanned using FIMO for consensus motifs from the TRANSFAC, JASPAR and MotifDB databases, with p-value threshold less than 1e-5 as described by S. Nepth et al's in "Circuitry and dynamics of human transcription factor regulatory networks" Cell, 150:1274-1286 (2012)).

Let $c_{i,j}$ be the number of TF j consensus motifs found within ±5 kb of the transcriptional start site (TSS) of gene i. False negatives would include distal binding locations outside of the ±5 kb window. False positives would be erroneous motif matches. Although many TFs can do both in the right circumstances, most TFs have tendency toward either activator or repressor activity. That is, if TF j is known to activate (or repress) some gene one can say with some confidence that TF j is an activator (repressor), so $w_{i,j} \geq 0$ ($w_{i,j} \leq 0$) for all i.

Of the 547 TFs, 299 were labeled as activators and 124 were labeled as repressors. The remaining TFs were labeled unknown since there was no conclusive evidence one way or the other.

Importantly, consensus motifs are cell-type invariant since they are based strictly on the linear genome. To obtain a skin-cell-specific regulatory picture, gene accessibility data was obtained (DNAse1 footprinting; if a narrow peak was found within ±5 kb of the genes TSS, the gene was deemed accessible, as this shows that some protein can bind here).

Let $a_1$ be the accessibility of gene i in skin cells, with 1 and 0 denoting accessible and inaccessible, respectively. Approximate $w_{i,j}$ as follows:

$$w_{i,j} := \pm a_i c_{i,j} \quad (1)$$

so that the magnitude of influence is equal to the number of observed consensus motifs, $c_{i,j}$, except when the gene is inaccessible in which case $w_{i,j}=0$. The sign of $w_{i,j}$ is determined from whether TF j is a known activator (positive) or repressor (negative).

In this disclosure, the objective is to mathematically identify a set of transcription factors that will directly reprogram a sample cell of a given cell type to a desired target cell type. The proposed approach couples data from bioinformatics with methods of mathematical control theory. More specifically, the framework separates into three parts: define the state, fit dynamics and define and evaluate the inputs. Each part is introduced below.

First, the structure and function observations of the initial and target cell types are used to define a comprehensive state representation of the genome. Next, model identification methods are applied to approximate the natural dynamics of the genome from data. To define the inputs, one can infer from bioinformatics where the transcription factor sets can influence the genome, then quantify controllability properties of the corresponding systems, specifically with respect to the target. Although the actual dynamics of the genome are undoubtedly nonlinear, dynamics are modeled using a discrete-time-invariant linear control system with the form $$x(k+1) = Ax(k) + Bu(k)$$

where $x(k+1)$ is an output vector in the state-space representation, $x(k)$ is a state vector in the state-space representation, A is the state transition matrix in the state-space representation, B is the input matrix in the state-space representation and $u(k)$ is the input vector in the state-space representation.

The state representation is the foundation of any control system and accordingly is critical for controllability analysis. Network science has emerged as a powerful conceptual paradigm for biological systems, with nodes typically representing genes or proteins, and edges representing regulatory relationships. An obstacle with this representation, however, is that there are over 20,000 genes in the human genome, thereby necessitating a dimension reduction. Naïve dimension reductions ignore inherent structural organization of the genome and obscure important intricacies of finer resolution. A comprehensive genome state representation should include aspects of both structure and function, and have low enough dimensions to be computationally reasonable. Along these lines, this disclosure proposes a biologically-inspired dimension reduction based on topologically associated domains.

Topologically associating domains (TADs) are continuous segments of DNA that interact spatially, displaying more intra- than inter-TAD activity. TADs can be observed from chromosome conformation assays, such as Hi-C, and have been shown to display shared transcription dynamics for genes within them.

To reduce the dimension, genes are grouped that are contained within the same TAD. N=2,245 TADs were identified that contain genes using a published algorithm that relies on DNA geometry measurements (high-resolution chromosome conformation capture, Hi-C).

Let tad(i):=k if gene i is contained within TAD k. Define the expression of TAD k from measurement m to be the sum of the expressions of genes within that TAD, i.e.:

$$x_{k,m} := \sum_{\substack{i \, s.t. \\ tad(i)=k}} g_{i,m} \quad (2)$$

The vector of all TAD activities at measurement m is denoted with a single subscript $x_m \in \mathbb{R}^N$, m=1, ..., 8. In summary, all measured TAD activity levels can be written $$\begin{pmatrix} x_{1,1} & x_{1,2} & \cdots & x_{1,8} \\ x_{2,1} & x_{2,2} & \cdots & x_{2,8} \\ \vdots & \vdots & \ddots & \vdots \\ x_{N,1} & x_{N,2} & \cdots & x_{N,8} \end{pmatrix} = \begin{pmatrix} | & | & & | \\ x_1 & x_2 & \cdots & x_8 \\ | & | & & | \end{pmatrix} \in \mathbb{R}^{N \times 8}. \quad (3)$$

Let $x_0 \in \mathbb{R}^N$ be an initial condition at time t=0, and let $x_* \in \mathbb{R}^N$ be a target condition to reach at time t=5 (40 hours).

Define the regulation weight $b_{k,j}$ of TF j on TAD k as the sum of regulation weights $w_{i,j}$ of genes within that TAD, i.e.:

$$b_{k,j} := \sum_{\substack{i \, s.t. \\ tad(i)=k}} w_{i,j} \quad (4)$$

Next, cell dynamics are modeled. Although qualitative models describing the changes in structure and proteomics that take place during the cell cycle have been found to be very useful, at present it seems that an all-encompassing quantitative model of such changes would be too complicated to contribute significantly to the understanding of cellular dynamics. Here it is argued that the development of some quantitative model of intermediate complexity holds great promise. The recent development of Hi-C has led to the identification of TADs and thus has opened up the possibility of developing models for cell dynamics organized around activity associated with TADs. Specifically, given that it is possible to measure the mRNA activity associated with individual genes at various stages of the cell cycle, one can collect the kind of data needed to develop a dynamical model. By comparing a gene's activity at successive points in time with the average value of the activity of that gene, one can expect to get a reasonably accurate model using a linear approximation.

In one example embodiment, measurements in this work were obtained from a colony of cells that had been synchronized by restricting their nutrient supply and then given a start signal. Measurements of gene activity were made every 8 hours and the activity of a TAD was taken to be the sum of the activities of all the genes it contains. Based on this data, an approximate evolution equation is constructed in the form $x(k+1)=Ax(k)$ to approximate the dynamical evolution of the TAD activity. The measurements used to construct the model consisted of the activity of all genes.

Let x be a 2245-dimensional vector whose components are the differences between the measured TAD activity and its average over a cycle. Within the limitations of the model, one can say that x at the end of some eight hour period is related to the TAD activity at the start of that eight hour period by some function $x(k+1)=f(x(k))$. However, because it is expected that this mapping depends on the stage the cell finds itself in at the start of the cycle, the function is time dependent. Given $x(0)$ and $x(1)$ there are many matrices A such that $x(1)=AX(0)$. In the example embodiment, the matrix that differs the least from the identity matrix is selected to serve as the state transition matrix. Other techniques, such as dynamic mode decomposition, can also be used to derive the state transition matrix A.

Because genome dynamics depend on the cell cycle, the state transition matrix, A, can also be defined as a time dependent state transition matrix $A(t) \in \mathbb{R}^{N \times N}$;

$$A(t) := \begin{cases} A_1 & \text{if } t \mod 5 = 0 \\ A_2 & \text{if } t \mod 5 = 1 \\ A_3 & \text{if } t \mod 5 = 2 \\ A_4 & \text{if } t \mod 5 = 3 \\ A_5 & \text{if } t \mod 5 = 4 \end{cases} \quad (5)$$

where $$A_m := I_N + \frac{(x_{m+1} - x_m)x_m^*}{x_m^* x_m} \in \mathbb{R}^{N \times N}, m = 1, 2, 3, 4 \quad (6)$$

$$A_5 := I_N + \frac{(x_1 - x_5)x_5^*}{x_5^* x_5} \in \mathbb{R}^{N \times N} \quad (7)$$

where * denotes transpose and $I_N$ is the N×N identity matrix. Given $x_m$ and $x_{m+1}$ there are many matrices $A_m$ such that $x_{m+1} = A_m x_m$ however eq (5) is the most "economical" in the sense that it differs from the identity as little as possible. This definition implies that $$x_2 = A_1 x_1, \quad (8)$$

$$x_3 = A_2 x_2, \quad (9)$$

$$x_4 = A_3 x_3, \quad (10)$$

$$x_5 = A_4 x_4, \quad (11)$$

$$x_1 = A_5 x_5. \quad (12)$$

Regulatory sets define where a given set of transcription factors could possibly influence the genome. The matrix B encodes where the control signal u[k] can influence the existing network defined by A. With $b_{k,j}$ representing the regulation weight of TF j on TAD k, one can define an input matrix $B_j$ for each TF j:

$$B_j := (b_{k,j}) \in \mathbb{N}^{N \times 1}, k = 1, \ldots, N. \quad (13)$$

The regulatory set for a set of transcription factors is the union of the regulatory sets for each individual transcription factor.

With a state transition matrix defined and input matrices defined for each TF, one can associate a discrete time differential equation with each TF in order to model the controllability of that transcription factor:

$$x(t+1) = A(t)x(t) + B_j u(t) \quad (14)$$

where t is the discrete time, x(t) is the state of the system at time t, and $u(t) \in \mathbb{R}^+$ is the input signal which in the model represents strength of TF input. The input vector, u(t), can then be solved for as will be further described below.

Figure 1A:
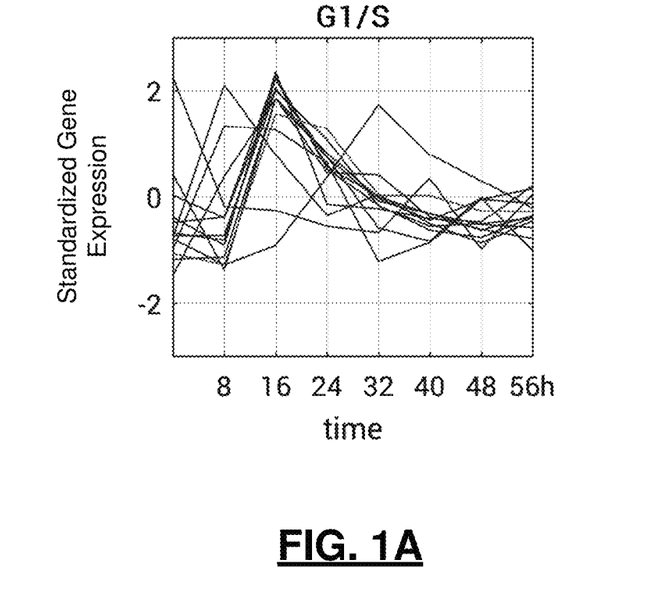
FIGS. 1A-1D are graphs showing the gene expression data for G1/S, S, G2 and G2/M, respectively, for a subset of known cell cycle marker genes.
Figure 1B:
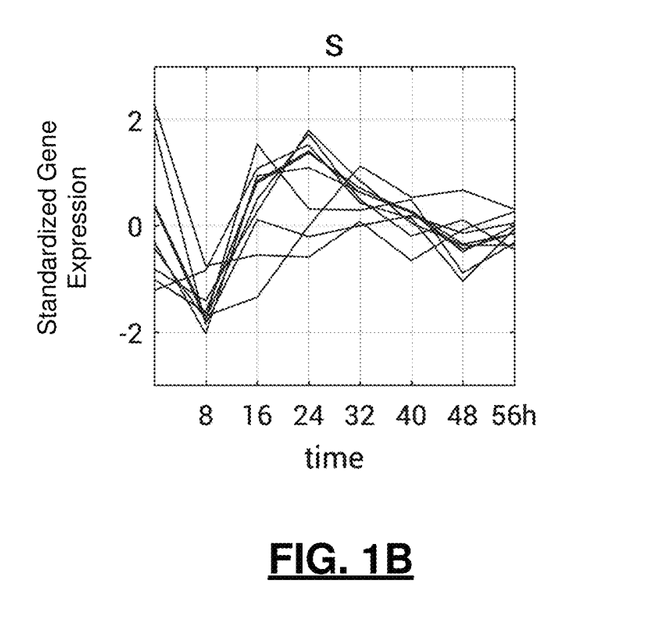
Figure 1C:
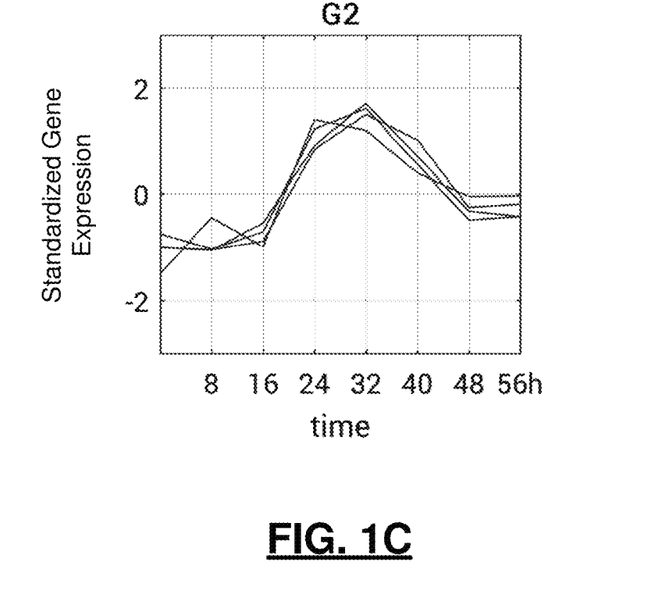
Figure 1D:
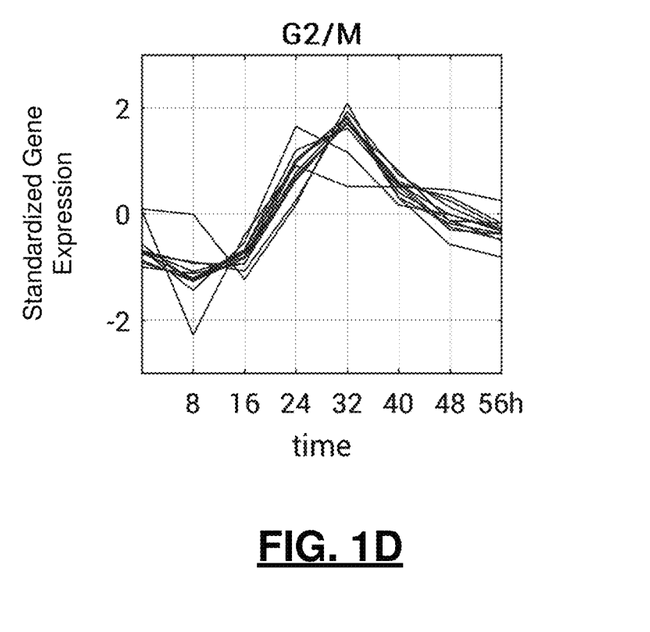
Figure 2:
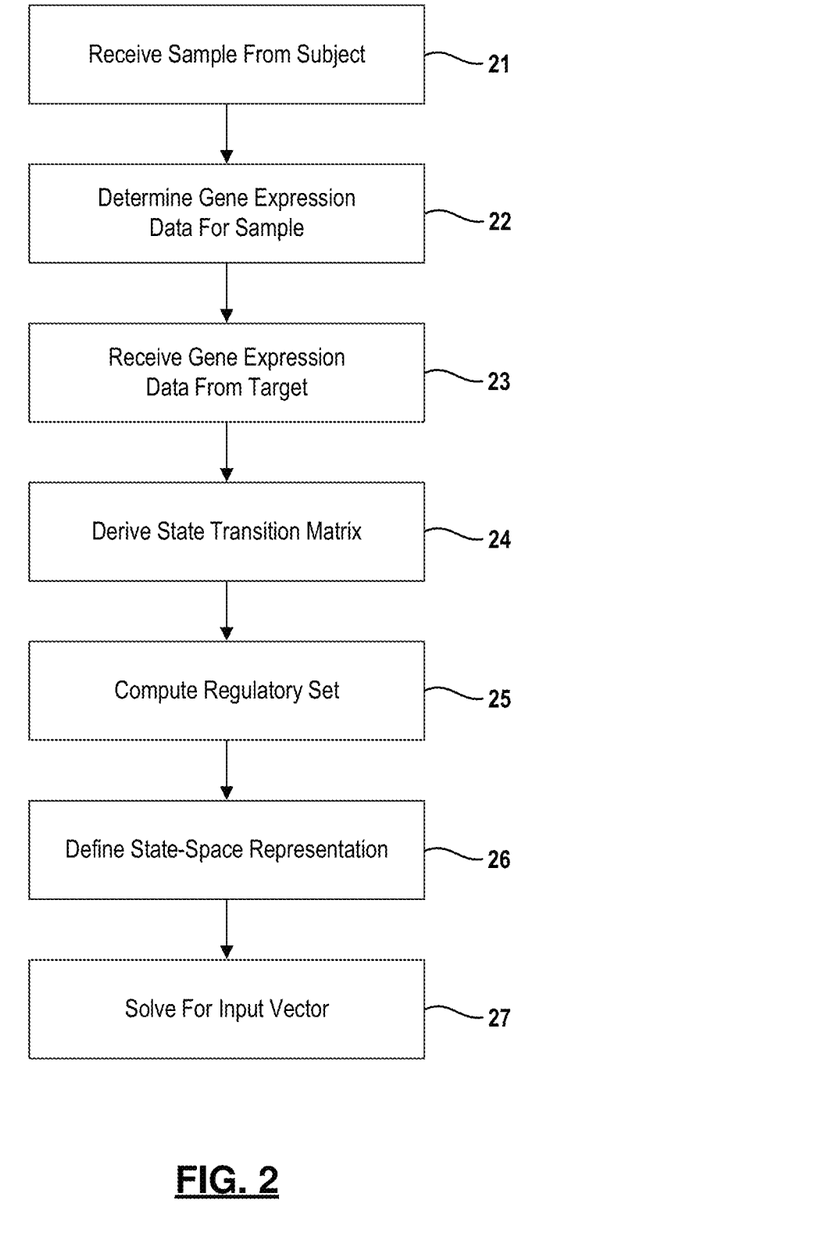
FIG. 2 is a flowchart depicting an overview of the proposed cell reprogramming method.

FIG. 2 provides an overview of the proposed method for reprogramming cells in accordance with this disclosure. A biological sample of a sample cell is first received at 21 from a subject, where the sample cell has a given cell type. The sample cell represents the initial state in the state-space model approach. In the example embodiment, the sample cell is a skin cell although other types of cells, such as embryonic cells, also fall within the scope of this disclosure.

From the biological sample, gene expression data is determined at 22 for the sample cell. In one embodiment, the gene expression data is further define as RNA-seq data which can be extracted from the biological sample using known DNA sequencing techniques. Other types of gene expression data include but are not limited to CAGE, Proteomics, Bru-seq, etc.

Likewise, gene expression data is received at 23 for a target cell having a target cell type, where the target cell type differs from the given initial cell type. In the example embodiment, target cell type is a muscle cell and the gene expression data for the target cell is also defined as RNA-seq data. Target cell types also include but are not limited to embryonic, cardiac, neuron, retinal, red blood cell, islets, T-cells, etc.

Next, the state transition matrix, A, which models cell dynamics is derived at 24, for example using the techniques set forth above. A regulatory set is then computed at 25 for one or more transcription factors, where a regulatory set quantifies influence of a given transcription factor on a genome. It is understood that a regulator set for a plurality of transcription factors can be formed by taking the union of the regulatory sets for each individual transcription factor.

Reprogramming of the sample cell to the target cell is expressed at 26 with a state-space representation of a linear system given in equation (14), where the gene expression data for the target cell serves as an output vector in the state-space representation, the gene expression data for the sample cell serves as a state vector in the state-space representation, the regulatory set for the given transcription factor serves as an input matrix in the state-space representation, and an input vector in the state-space representation represents the given transcription factor.

Lastly, the input vector in the state-space representation is solved for as indicated at 27. In a simplified embodiment, cells may be reprogrammed directly using one transcription factor. Because an input matrix B has been defined for each transcription factor, an input vector is determined for each transcription factor using the corresponding input matrix. The values for the input vector may be determined, for example using a least squares method executed in MATLAB. Other regression techniques may also be used to solve for the input vector in the state-space representation. The transcription factor which results in a cell that is closest to the target cell type is deemed the solution.

Imposing some biology into the algorithm, it is known that transcription factors used in direct reprogramming are almost always up-regulated in the target state. In order to choose transcription factors most reflective of reality and minimize computation time, subsets of transcription factors can be chosen for each direct reprogramming calculation before computation.

In an example embodiment, transcription factors are selected for the subset of transcription factors if they meet the following criteria. First, the transcription factor is expressed in the target cell. For example, greater than 4 RPKM expression in target state. This criterion helps to minimize potential noise in genomic signatures in TF subset selection. Second, the expression of the transcription factor in the target state must be greater than some threshold (e.g., 10) as compared to the initial state. This criterion is used to select transcription factors that are up-regulated in the target state. Rather than solving for all 300+ transcription factors, calculations can be made for only the transcription factors which meet the threshold criteria above. Other types of thresholding criteria are envisioned and fall within the broader aspects of this disclosure.

In another aspect, different transcription factors can be input to the cell at different points through the cell cycle. In an example embodiment, there are five possible input times (i.e., 0, 8, 16, 24, and 32 hours) although more or less input times are possible. Once a transcription factor is input, it is assumed that it continue to influence the system until the end of the cell cycle (e.g., 40 hours).

Continuing with the state-space representation of equation (14), the input vector may be solved for as follows:

$$x(3) = A_3 A_2 A_1 x_0 + A_3 A_2 Bu(0) + A_3 Bu(1) + Bu(2) \quad (15)$$

Assume u(t):=$\bar{u}$ is constant for all t. Then Eqn (23) can be written $$x(3) = A_3 A_2 A_1 x_0 + C\bar{u}, \quad (16)$$

where $$C := (A_3 A_2 + A_3 + I_N) B$$

and one seeks the control u that minimizes the distance between x(3) and the target $x_*$:

$$\min_{\bar{u}} \|x_* - A_3 A_2 A_1 x_0 - C\bar{u}\|. \quad (17)$$

It can be seen that an exact solution exists if $$x_* - A_3 A_2 A_1 x_0 \in \mathrm{span}(C), \quad (18)$$

and is given by $$A_3 A_2 A_1 x_0 + C\bar{u} = x_*, \quad (19)$$

$$C\bar{u} = x_* - A_3 A_2 A_1 x_0 \quad (20)$$

$$\bar{u} + C^\dagger (A_3 A_2 A_1 x_0) \quad (21)$$

where $C^\dagger$ denotes the Moore-Penrose pseudoinverse of the matrix C, computed using the singular value decomposition of C. Even when Eqn (26) is not satisfied, it is well established that the control (29) solves (25).

Define $$\mu_3 := \|(I_N - CC^\dagger)(x_* - A_3 A_2 A_1 x_0)\| \quad (22)$$

For $\mu_3$ for B(t), the solution to Eqn. (14) after t=3 time steps (i.e., 24 hours) is $$x(3) = A_3 A_2 A_1 x_0 + A_3 A_2 B(0) u(0) + A_3 B(1) u(1) + B(2) u(2) \quad (23)$$

Assume u(t):=$\bar{u}$ is constant for all t. Then Eqn (23) can be written $$x(3) = A_3 A_2 A_1 x_0 + C\bar{u}, \quad (24)$$

where $$C := A_3 A_2 B(0) + A_3 B(1) + B(2)$$

One seeks the control $\bar{u}$ that minimizes the distance between x(3) and the target $x_*$:

$$\min_{\bar{u}} \|x_* - A_3 A_2 A_1 x_0 - C\bar{u}\| \quad (25)$$

It can be seen that an exact solution exists if $$x_* - A_3 A_2 A_1 x_0 \in \mathrm{span}(C), \quad (26)$$

and is given by $$A_3 A_2 A_1 x_0 + C\bar{u} = x_* \quad (27)$$

$$C\bar{u} = x_* - A_3 A_2 A_1 x_0 \quad (28)$$

$$\bar{u} = C^\dagger (x_* - A_3 A_2 A_1 x_0) \quad (29)$$

where $C^\dagger$ denotes the Moore-Penrose pseudoinverse of the matrix C. Even when Eqn (26) is not satisfied, it is well established that the control (29) solves (25).

Define $$\mu_3 := \|(I_N - CC^\dagger)(x_* - A_3 A_2 A_1 x_0)\| \quad (30)$$

In the example above, the cell cycle is concluded after three steps (i.e., 24 hours). It is readily understood that this approach may be extended to more or less steps. Again, the computation above can be made for each transcription factor (or a subset of transcription factors), where the same transcription factor is introduced at each step, and the transcription factor which results in a cell that is closest to the target cell type is deemed the solution.

Alternatively, a different transcription factor can be introduced at each step. The computation for the input vector is then made for each combinational sequence of transcription factors. For example, assuming three transcription factors $TF_1$, $TF_2$ and $TF_3$ and two steps, possible combinational sequences are as follows:

| t = 0 | t = 1 |
|---|---|
| $TF_1$ | $TF_2$ |
| $TF_1$ | $TF_3$ |
| $TF_2$ | $TF_1$ |
| $TF_2$ | $TF_3$ |
| $TF_3$ | $TF_1$ |
| $TF_3$ | $TF_2$ |
| | $TF_{2,3}$ |
| ... | ... |

In this case, the input vector is determined for each possible combinational sequence and the combinational sequence which results in a cell that is closest to the target cell type is deemed the solution.

With the method and motivation for computation established, the proposed algorithm is verified by testing for detection of known reprogramming TFs, then explored for optimization of TF addition over time. For illustration purposes, the reprogramming lineages selected includes fibroblast to Myotube, and fibroblast to embryonic stem cell.

Since Weintraub's original reprogramming experiment in 1989, it has been established and confirmed that for fibroblast to myotube conversion a single TF, MyoD, is needed. The proposed reprogramming method was able to successfully select MyoD from a set of 332 TFs as the best TF for fibroblast to myotube conversion, thus partially confirming the programs validity.

For proposed reprogramming method, existing timeseries fibroblast data was used as the initial state and RNA-seq data on human Myotube cells as a target state. Out of the 332 possible TFs scored, a subset of 7 TFs computationally passed initial thresholding, with greater than 10-fold upregulation and greater than 2 RPKM expression in the target state. From this subset, TF MyoD received the highest score ([1−mu3/dzK]*$10^3$) with 58.82. Other TFs within this subset with notable scores include PITX2(41.33), PKNOX2 (40.39), and SIX2 (39.34). Note that PKNOX2 and Six2 are scored as possible activators here, though their true respective TF property is less definite (no strong source for labelling as either activator or repressor). The table below shows the TFs plotted with significant scoring information shown.

| Rank | TF | Score (*$10^3$) |
|---|---|---|
| 1 | MyoD | 58.82 |
| 2 | PITX2 | 41.33 |
| 3 | PKNOX2+ | 40.39 |

-continued

| | | |
|---|---|---|
| 4 | Six2+ | 39.34 |
| 5 | EN1 | 0 |
| 6 | HOXB3 | 0 |
| 7 | PKNOX2- | 0 |
| 8 | Six2- | 0 |

| Myotube | | $\mu$ |
|---|---|---|
| 1 | MYOG | 1753 |
| | MYOD1 | 1065 |
| | PKNOX2 | 797 |
| | SIX2 | 745 |
| | PITX2 | 744 |

For further confirmation, it was sought to determine if the proposed reprogramming method would extract the Yamanaka factors for fibroblast to ESC (iPSC) conversion. Though not as clear cut as FIB to MT conversion, the proposed reprogramming method did successfully select factors known to reprogram FIBS to ESCs.

| Rank | TF | Score (*10³) |
|---|---|---|
| 1 | MYCN | 1.17 |
| 2 | NANOG | 1.15 |
| 3 | GLI1 | 1.09 |
| 4 | NR6A1 | 0.94 |
| 5 | ZFP42 | 0.89 |
| 6 | SOX2 | 0.81 |
| 7 | TERF1+ | 0.76 |
| 8 | OTX2 | 0.29 |
| 9 | FOXD3 | 0 |
| 10 | KLF15 | 0 |
| 11 | POU5F1 | 0 |
| 12 | ZIC2 | 0 |
| 17 | TERF1- | 0 |

| ESC | | $\mu$ |
|---|---|---|
| 1 | MYCN | 2634 |
| | ZVP42 | 2453 |
| | NANOG | 2013 |
| | OTX2 | 1628 |
| | SOX2 | 1025 |

ESC RNA-Seq Data for this Analysis was Gathered from ENCODE (GSM591652).

Initial analysis scored TFs individually, resulting in 15 candidate TFs from an original set of 332 possible TFs. Notable pluripotency marker TFs within this subset included NANOG, SOX2, POU5F1, and ZFP42 (with pluripotency marker family TFs including KLF15 and MYCN). From this subset, MYCN scored the highest (1.17) with NANOG scoring $2^{nd}$ (1.15), SOX2 $6^{th}$ (0.81), and POU5F1 $11^{th}$ (0). Though no TFs scored exceptionally well, known TFs for FIB to ESC conversion were recovered.

Fibroblast to Embryonic Stem Cell—Individual

| Rank | TF | Score (*10³) |
|---|---|---|
| 1 | NANOG + POU5F1 + SOX2 | 2.16 |
| 2-11 | NANOG + POU5F1 + other | 2.05-1.97 |
| 12 | SOX2 + POU5F1 + MYCN | 1.68 |
| 13-15 | SOX2 + POU5F1 + other | 1.63-1.46 |
| 16-286 | other | 1.35-0 |

| ESC | | $\mu$ |
|---|---|---|
| 3 | MYCN, NANOG, POU5F1 | 2840 |
| | MYCN, ZFP42, POU5F1 | 2801 |
| | MYCN, NANOG, ZFP42 | 2747 |
| | MYCN, OTX2, ZFP42 | 2746 |
| | MYCN, SOX2, ZFP42 | 2746 |

Knowing that no individual TF has thus far been found to achieve full fibroblast to ESC conversion, testing was done to determine whether the use of a cocktail of TFs would give better scores, and results (Yamanaka Factors).

From the 15 TFs passing initial thresholding, all possible combinations of three TFs were scored. In this analysis, more reflective of reality, known TF for FIB to ESC reprogramming combinations scored much better. Specifically, POU5F1 scored much better when used in combination with other TFs. The top combination scored was POU5F1, NANOG, and SOX2 (2.16), with the following 10 highest scores coming from POU5F1 with NANOG and a $3^{rd}$ TF (2.05-1.97). The next highest score came from POU5F1, SOX2 and MYCN (1.68), with POU5F1, SOX2 and a $3^{rd}$ TFs as the next 3 (1.63-1.46).

| Rank | TF | Score (*10³) |
|---|---|---|
| 1 | NANOG + SOX2 + POU5F1 [5, 5, 2] | 17.57 |
| 2 | NANOG + SOX2 + POU5F1 [5, 5, 1] | 16.22 |
| 3 | NANOG + SOX2 + POU5F1 [5, 4, 2] | 14.42 |
| 4 | NANOG + SOX2 + POU5F1 [5, 5, 3] | 14.29 |
| 5 | NANOG + SOX2 + POU5F1 [5, 1, 2] | 14.19 |
| 6 | NANOG + SOX2 + POU5F1 [5, 2, 2] | 14.19 |
| 7 | NANOG + SOX2 + POU5F1 [5, 3, 2] | 14.19 |
| 8 | NANOG + SOX2 + POU5F1 [5, 4, 1] | 13.34 |

Consider inputting different TFs at different points throughout the cell cycle. In an example embodiment, there are five possible input times: 0, 8, . . . , 32 hours, and once a TF is input we assume it continues to influence the system until the final time of 40 hours. The analysis is restricted to three known factors {Pou5f1, Sox2, Nanog}. This gives $5^3=125$ possible regimes to input the TFs; e.g., Pou5F1, Sox2, Nanog at times 0,0,0, or 0,0,8, or 0,0,16, or . . . or 32,32,24 or 32,32,32.

Inputting a TF at time $t_*$ can be viewed mathematically as requiring u(t)=0 for all $t<t_*$. An analogous view is to define a time-dependent $B_j(t)$, where (with abuse of notation)

$$B_j(t) := \begin{cases} 0 & t < t_* \\ B_j & t_* \leq t \end{cases} \quad (31)$$

with the time independent $B_j$ as defined above. The computation of $\mu_3$ naturally extends to time-dependent $B_j(t)$. All 125 regimes were scored.

A key benefit of the proposed reprogramming method is that it utilizes dynamic time series data, allowing for analysis of combinations of TFs added at different times.

To test this analysis, we explored the best potential way to implement POU5F1, NANOG, and SOX2 to a population of synchronized fibroblast for FIB to ESC conversion. This combination both scored well in our combination analysis and is a known combination for FIB to ESC conversion. Our algorithm computes starting at t0 (G0/G1) and iterates over 5 times steps, covering a full cell cycle. All possible time-dependent combinations of these TFs were computed.

The analysis shows that addition of POU5F1 early in the cell cycle (G0/1), later addition of NANOG and SOX2 (G2)

would work best for iPSC conversion. The top scoring combination suggests adding POU5F1 at t2 (G1), with NANOG and SOX added later in G2 at t5.

| Rank | TF | Score (*$10^3$) |
|---|---|---|
| 1 | HMBOX | 5.06 |
| 2 | KLF15 | 3.76 |
| 3 | ERG− | 3.32 |
| 4 | GATA4 | 0 |
| 5 | GATA6 | 0 |
| 6 | HLF | 0 |
| 7 | PGR | 0 |
| 8 | SOX17 | 0 |
| 9 | ERG+ | 0 |

The proposed reprogramming method has been shown to correctly predict transcription factors needed for a number of human fibroblast reprogramming regimes, and has discovered potentially useful TFs that can possibly increase reprogramming efficiency. This analysis can be implemented for any human fibroblast reprogramming experiment to best predict possible TFs, greatly reducing guess-and-check, wet lab methods. Novel analysis on the implementation of TF combinations at different times during reprogramming increases reprogramming efficiency. This framework can be expanded to any human cell type, given initial state time series RNA-seq data, covering a full cell cycle from a population of synchronized cells, and target state RNA-seq data.

The cell is not a static object, so assuming all cells of a cell-type have the exact same transcription oversimplifies a cell's true function. Times series data on a synchronized population of cells allow for the best analysis on how the cell operates overtime.

A large contributor to the scores achieved by the proposed reprogramming method is that a TF relies on how a TF affects a gene, whether it is an activator or a repressor. Currently, the proposed reprogramming method label a TF as either an activator or a repressor, based on average activity, and weights the effect on transcription solely on the number of binding sites. In reality, TFs can vary whether they are activators or repressors on a case by case basis, and the relative effect on the transcription can vary as well.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for reprogramming cells of a subject, comprising:
   receiving a biological sample of a sample cell from the subject, where the sample cell has a given cell type;
   determining gene expression data for the sample cell from the biological sample;
   receiving gene expression data for a target cell having a target cell type, where the target cell type differs from the given cell type;
   deriving a state transition matrix which models cell dynamics;
   computing a regulatory set for a given transcription factor, where the regulatory set quantifies influence of the given transcription factor on a genome;
   expressing reprogramming of the sample cell to the target cell with a state-space representation of a linear system, where the gene expression data for the target cell serves as an output vector in the state-space representation, the gene expression data for the sample cell serves as a state vector in the state-space representation, the regulatory set for the given transcription factor serves as an input matrix in the state-space representation, and an input vector in the state-space representation represents the given transcription factor;

solving for the input vector in the state-space representation; and introducing the given transcription factor into a particular cell of the subject, where the particular cell has the given cell type.

2. The method of claim 1 wherein determining gene expression data for the cell includes grouping genes within same topologically associated domains; and forming the state vector from the grouped genes.

3. The method of claim 2 further comprises grouping genes within same topologically associated domains using chromosome conformation capture techniques.

4. The method of claim 1 wherein the gene expression data for the sample cell is further defined as RNA-seq data.

5. The method of claim 1 wherein computing a regulatory set for a given transcription factor further comprises computing a regulator set for each of a plurality of transcription factors and joining the plurality of regulatory sets to form the input matrix.

6. The method claim 1 wherein solving for the input vector further comprises determining values for the input vector that minimize distance between the sample cell and the target cell.

7. The method of claim 6 further comprises determining values for the input vector using a least squares method.

8. The method of claim 1 wherein expressing reprogramming of the sample cell includes defining the state-space representation at two or more discrete times, where the two or more discrete times signify different points in a cell cycle and the given transcription factor can be introduced into a cell at any of the two or more discrete times.

9. The method of claim 8 wherein solving for the input vector further comprises identifying a subset of transcription factors, determining each possible sequence in which the transcription factors in the subset of transcription factors can be introduced into a cell, and solving for the input vector for each possible sequence of transcription factors in the subset of transcription factors.

10. A method for reprogramming cells of a subject, comprising:

determining gene expression data for a sample cell from the subject by grouping genes within same topologically associated domains, where the sample cell has a given cell type;

determining gene expression data for a target cell having a target cell type, where the target cell type differs from the given cell type;

deriving a state transition matrix which models cell dynamics;

computing a regulatory set for a given transcription factor, where the regulatory set quantifies influence of the given transcription factor on a genome;

expressing reprogramming of the sample cell to the target cell with a state-space representation of a linear system, where the gene expression data for the target cell serves as an output vector in the state-space representation, the gene expression data for the sample cell serves as a state vector in the state-space representation, the regulatory set for the given transcription factor serves as an input matrix in the state-space representation, and an input vector in the state-space representation represents the given transcription factor;

solving for the input vector in the state-space representation by determining values for the input vector that minimize distance between the sample cell and the target cell; and introducing the given transcription factor into a particular cell of the subject, where the particular cell has the given cell type.

11. The method of claim 10 further comprises grouping genes within same topologically associated domains using chromosome conformation capture techniques.

12. The method of claim 10 wherein the gene expression data for the sample cell is further defined as RNA-seq data.

13. The method of claim 10 wherein computing a regulatory set for a given transcription factor further comprises computing a regulator set for each of a plurality of transcription factors and joining the plurality of regulatory sets to form the input matrix.

14. The method of claim 10 wherein expressing reprogramming of the sample cell includes defining the state-space representation at two or more discrete times, where the two or more discrete times signify different points in a cell cycle and the given transcription factor can be introduced into a cell at any of the two or more discrete times.

15. The method of claim 14 wherein solving for the input vector further comprises identifying a subset of transcription factors, determining each possible sequence in which the transcription factors in the subset of transcription factors can be introduced into a cell, and solving for the input vector for each possible sequence of transcription factors in the subset of transcription factors.

* * * * *

UNITED STATES PATENT AND TRADEMARK OFFICE
CERTIFICATE OF CORRECTION

PATENT NO. : 10,672,501 B2
APPLICATION NO. : 15/678142
DATED : June 2, 2020
INVENTOR(S) : Indika Rajapakse et al.

Page 1 of 1

It is certified that error appears in the above-identified patent and that said Letters Patent is hereby corrected as shown below:

In the Claims

At Column 15, Claim number 6, Line number 25, after "method", insert --of--

Signed and Sealed this
Twenty-ninth Day of September, 2020

Andrei Iancu
*Director of the United States Patent and Trademark Office*